US009820733B2

(12) United States Patent
Nolan et al.

(10) Patent No.: US 9,820,733 B2
(45) Date of Patent: *Nov. 21, 2017

(54) MOULDED IN PLACE SEAL PLUG AND SUTURE ANCHOR

(71) Applicant: Cardiac Pacemakers, Inc., St. Paul, MN (US)

(72) Inventors: Daragh Nolan, Via Youghal (IE); James M. English, Cahir (IE); John O'Rourke, Tip (IE); Sean Walsh, Clare (IE); John H. Tangren, Lino Lakes, MN (US); Brian D. Allen, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 257 days.

This patent is subject to a terminal disclaimer.

(21) Appl. No.: 14/327,824

(22) Filed: Jul. 10, 2014

(65) Prior Publication Data

US 2015/0018877 A1    Jan. 15, 2015

Related U.S. Application Data

(60) Provisional application No. 61/845,507, filed on Jul. 12, 2013.

(51) Int. Cl.
| A61N 1/375 | (2006.01) |
| A61B 17/04 | (2006.01) |
| B29C 45/14 | (2006.01) |
| B29C 45/00 | (2006.01) |
| A61N 1/39  | (2006.01) |
| A61N 1/362 | (2006.01) |

(52) U.S. Cl.
CPC .......... *A61B 17/0401* (2013.01); *A61N 1/362* (2013.01); *A61N 1/375* (2013.01); *A61N 1/3752* (2013.01); *A61N 1/39* (2013.01); *A61N 1/3968* (2013.01); *B29C 45/0001* (2013.01); *B29C 45/14467* (2013.01)

(58) Field of Classification Search
CPC ........ A61N 1/375; A61N 1/39; A61N 1/3968; A61N 1/362; A61N 1/3752; A61B 17/0401; B29C 45/0001; B29C 45/14467
USPC ............................................ 607/5, 9, 36, 37
See application file for complete search history.

(56) References Cited

U.S. PATENT DOCUMENTS

| 3,822,707 A | 7/1974 | Adducci |
| 3,908,668 A | 9/1975 | Bolduc |
| 4,072,154 A | 2/1978 | Anderson et al. |
| 4,105,037 A | 8/1978 | Richter et al. |
| 4,141,752 A | 2/1979 | Shipko |
| 4,180,078 A | 12/1979 | Anderson |
| 4,461,194 A | 7/1984 | Moore |
| 4,479,489 A | 10/1984 | Tucci |
| 5,012,807 A | 5/1991 | Stutz, Jr. |
| 5,086,773 A | 2/1992 | Ware |

(Continued)

*Primary Examiner* — Michael Carey
(74) *Attorney, Agent, or Firm* — Schwegman Lundberg & Woessner, P.A.

(57) ABSTRACT

An implantable pulse generator includes a device housing containing pulse generator circuitry and a header molded to the device housing. The header can be formed of an epoxy header material. A header component can have a first part molded in the header material to fix the header component to the header at a surface of the header and a second part extending out of the header material.

8 Claims, 7 Drawing Sheets

(56) References Cited

U.S. PATENT DOCUMENTS

| | | |
|---|---|---|
| 6,817,905 B2 | 11/2004 | Zart et al. |
| 7,155,283 B2 | 12/2006 | Ries et al. |
| 7,955,543 B2 | 6/2011 | Deininger et al. |
| 8,103,348 B1 | 1/2012 | Coffed et al. |
| 8,315,700 B2 | 11/2012 | Citron et al. |
| 9,242,107 B2 * | 1/2016 | Nolan ................ A61N 1/3752 |
| 2002/0107555 A1 | 8/2002 | Rusin et al. |
| 2002/0138114 A1* | 9/2002 | Gramse ................ A61N 1/375 607/37 |
| 2004/0122481 A1 | 6/2004 | Tidemand et al. |
| 2006/0015150 A1 | 1/2006 | Rusin et al. |
| 2011/0160808 A1* | 6/2011 | Lyden .................... A61N 1/37 607/63 |
| 2012/0090161 A1* | 4/2012 | Biggs, Jr. ............ A61N 1/3752 29/593 |

* cited by examiner

MOULDED IN PLACE SEAL PLUG AND SUTURE ANCHOR

CROSS-REFERENCE TO RELATED APPLICATION

This application claims priority to U.S. Provisional Application 61/845,507, filed Jul. 12, 2013, which is herein incorporated by reference in its entirety.

TECHNICAL FIELD

The present invention relates to implantable medical devices. More specifically, the invention relates to molded headers for implantable medical devices.

BACKGROUND

Various physiological functions can be managed and/or monitored using medical devices. Many such medical devices are implantable in a human body, such as implantable cardioverter-defibrillators (ICDs) or pacemakers. Such devices typically include a housing enclosing the device and may or may not include one or more medical electrical leads that can transmit electrical signals to and/or from a sensor, electrode, or other electrical component at a distal end of the medical electrical lead. For example, such devices have been used in association with cardiac rhythm management, which can include cardiac pacing, cardiac defibrillation, and/or cardiac therapy, among other procedures.

In some such devices, the housing can isolate internal components from conductive bodily fluids after implant. Various designs for such housings are known in the art, some of which include headers for connecting the medical electrical leads to the device. There exists a need for alternative designs for headers and associated components for such implantable medical devices.

SUMMARY

Disclosed herein are various embodiments of medical devices and methods of molding components on a surface of a header of a medical device.

In Example 1, a method of molding a header of an implantable pulse generator includes providing a mold having an inner surface defining a header mold cavity, positioning a device housing at least partially in the mold adjacent the header mold cavity, and positioning a header component in the mold such that a first part of the header component is positioned in the header mold cavity and a second part of the header component is adjacent the mold. Header material is injected into the header mold cavity to form the header such that the header is attached to the device housing and the header component is attached to the header at a surface of the header and extending out of the header when the header material solidifies.

In Example 2, the method according to Example 1, wherein the mold comprises silicone and the header material comprises epoxy.

In Example 3, the method according to any of Examples 1-2, wherein pulse generator circuitry within the device housing is connected to electrical contacts in the header via a plurality of electrical leads prior to injecting the header material.

In Example 4, the method according to any of Examples 1-3, wherein the header component is a seal plug for sealing a set screw hole of the header, and wherein the seal plug has a deformable slit extending through a top of the seal plug through which a tool can be inserted and that is substantially closed to seal and limit fluid flow through the seal plug when the tool is removed.

In Example 5, the method according to Example 4, wherein the seal plug has a substantially frustoconical surface and the header material covers some but not all of the frustoconical surface.

In Example 6, the method according to any of Examples 4-5, and further including positioning a core in the header mold cavity, wherein the seal plug is held between the core and the mold with a portion of the seal plug seated in a core hole of the core prior to injecting the header material.

In Example 7, the method according to Example 6, wherein an interface between the seal plug and the core hole is substantially free of medical adhesive.

In Example 8, the method according to Example 1, wherein the header component is a suture anchor for attaching the header to tissue in a medical patient.

In Example 9, the method according to Example 8, wherein the suture anchor comprises a line having a first end anchored in the header material, a second end anchored in the header material, and a loop between the first and second ends extending out of the header material.

In Example 10, the method according to Example 9, and further including forming a first knot in a first end of the line and a second knot in a second end of the line prior to positioning the suture anchor in the mold.

In Example 11, the method according to Example 9, wherein the line comprises a braided thread.

In Example 12, the method according to any of Examples 8-11, wherein the suture anchor comprises a flexible membrane that can be pierced by a suture needle.

In Example 13, the method according to Example 12, wherein the flexible membrane is porous.

In Example 14, the method according to any of Examples 8-13, wherein the suture anchor is a first suture anchor on a first edge of the header, and the method further includes positioning a second suture anchor in the mold such that the second suture anchor is attached via the header material on the surface of the header at a second edge of the header that is different than the first edge of the header.

In Example 15, an implantable pulse generator includes a device housing containing pulse generator circuitry and a header molded to the device housing. The header can be formed of an epoxy header material. A header component can have a first part molded in the header material to fix the header component to the header at a surface of the header and a second part extending out of the header material.

In Example 16, the implantable pulse generator according to Example 15, wherein the header component is a seal plug having a deformable slit extending through a top of the seal plug through which a tool can be inserted and that is substantially closed to seal and limit fluid flow through the seal plug when the tool is removed.

In Example 17, the implantable pulse generator according to Example 16, wherein the seal plug is positioned in a set screw hole that comprises a header body hole defined by the epoxy header material of the header, and wherein a distance across an outer portion of the header body hole is less than a distance across an inner portion of the header body hole.

In Example 18, the implantable pulse generator according to Example 15, wherein the header component is a suture anchor for attaching the header to tissue in a medical patient.

In Example 19, the implantable pulse generator according to any of Examples 15-18, wherein an interface between the header component and the header is substantially free of medical adhesive.

In Example 20, a pulse generator for a cardiac rhythm management system can include a device housing and a header molded to the device housing. The header can be formed of an epoxy header material that defines a set screw hole. A distance across an outer portion of the set screw hole is less than a distance across an inner portion of the set screw hole. A set screw can be positioned in the header and aligned with the set screw hole. A seal plug can have a deformable slit extending through the seal plug for receiving a tool to tighten the set screw. The seal plug can be molded in the epoxy header material at a surface of the header to fix the seal plug to the header with a plug top of the seal plug extending out of the surface of the header.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
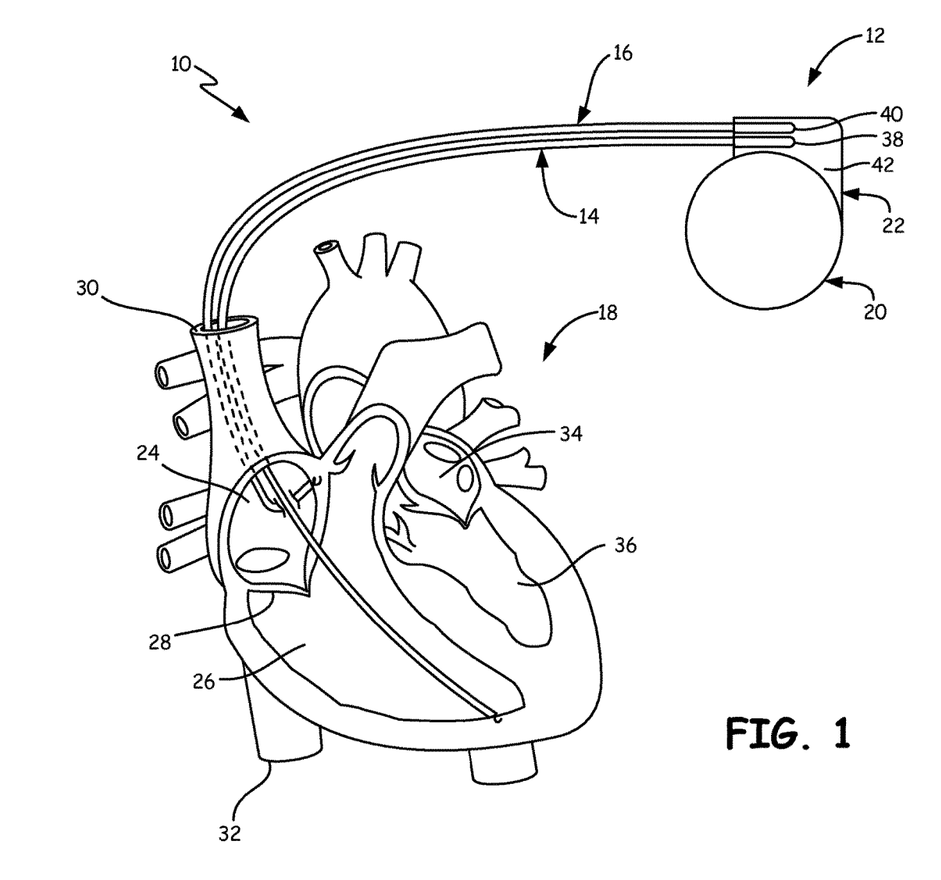
FIG. 1 is a schematic view of a cardiac rhythm management (CRM) system according to one embodiment of the present invention.

FIG. 1 is a schematic view of a cardiac rhythm management (CRM) system 10 according to one embodiment. As shown in FIG. 1, the CRM system 10 includes a pulse generator 12 coupled to a plurality of leads 14 and 16 deployed in a patient's heart 18. The pulse generator 12 includes a housing 20 and a header 22 mounted on the housing 20. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. As further shown, the heart 18 includes a left atrium 34, which receives oxygenated blood from the lungs, and a left ventricle 36, which pumps the oxygenated blood to the body.

The leads 14 and 16 are medical electrical leads that operate to convey electrical signals and stimuli between the heart 18 and the pulse generator 12. The header 22 of the pulse generator 12 is an output terminal header with cores 38 and 40 substantially encapsulated in a header body 42. The cores 38 and 40 are output terminal cores for receiving proximal ends of the leads 14 and 16, respectively. In the illustrated embodiment, a distal end of the lead 14 is implanted in the right ventricle 26, and a distal end of the lead 16 is implanted in the right atrium 24. In other embodiments, the CRM system 10 may include additional leads, e.g., a lead extending into a coronary vein for stimulating the left ventricle in a bi-ventricular pacing or cardiac resynchronization therapy (CRT) system. As shown, the leads 14 and 16 enter the superior vena cava 30, and are implanted in the right ventricle 26 and right atrium 24, respectively.

The pulse generator 12 can be implanted subcutaneously within an implantation location or pocket in the patient's chest or abdomen. The pulse generator 12 can be any implantable medical device known in the art, or later developed, for delivering an electrical therapeutic stimulus to the patient. In various embodiments, the pulse generator 12 can be a neurostimulation device, a pacemaker, a CRT device, an implantable cardiac defibrillator, and/or can include both pacing, CRT and/or defibrillation capabilities (e.g., a CRT-D device).

In some embodiments the CRM system 10 can be configured to stimulate cardiac tissue and/or sense certain physiological attributes of the heart. However, in discussing embodiments of the present disclosure, reference is made primarily to stimulating body tissues. Those of ordinary skill in the art will recognize that some or all of the configurations can also be used to receive electrical signals from the body.

Figure 2A:
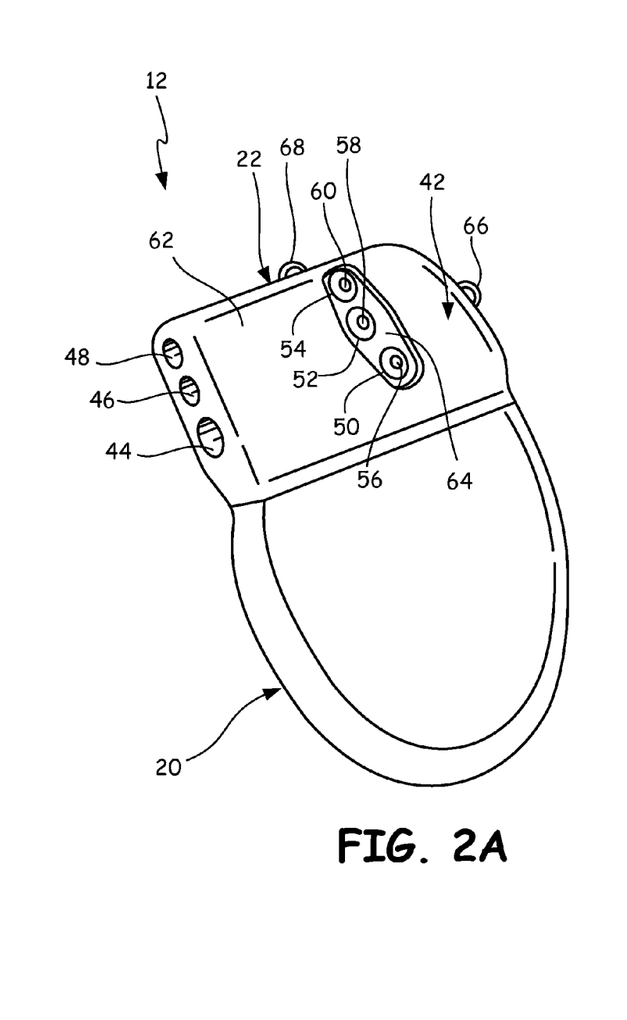
FIG. 2A is a perspective view of one embodiment of a pulse generator for use in the CRM system of FIG. 1, with an opaque header body.

FIG. 2A is a perspective view of the pulse generator 12 with the header 22 having an opaque header body 42. The header 22 has a plurality of receptacles 44, 46, and 48 in the header body 42. The receptacles 44, 46, and 48 are terminal holes that allow lead terminal pins of leads, such as the leads 14 and 16 (shown in FIG. 1) to be inserted into cores, such as the cores 38 and 40 (shown in FIG. 1). Because the header body 42 is opaque, the cores 38 and 40 are not visible in FIG. 2A.

The header 22 also has a plurality of holes 50, 52, and 54, which are set screw holes that allow access to set screws (not shown in FIG. 2A) that can be tightened to fasten the lead terminals of the leads 14 and 16 in the cores 38 and 40. Plugs 56, 58, and 60 are seal plugs that are inserted into and seal the holes 50, 52, and 54, respectively.

In the illustrated embodiment, the header body 42 has an outer surface 62 and an indented surface 64 sunken below the outer surface 62. The outer surface 62 and the indented surface 64 both face substantially outward from the header body 42. The indented surface 64 surrounds the holes 50, 52, and 54. The plugs 56, 58, and 60 are positioned in the holes 50, 52, and 54 so as to extend above the indented surface 64 but, in the illustrated embodiment, do not extend substantially above the outer surface 62.

The header body 42 can also have one or more suture anchors 66 and 68 that can be used to hold the pulse generator 12 in place when implanted in a human body of a medical patient. Sutures or other fasteners can attach one or more of the suture anchors 66 and 68 of the header 22 to tissue of the medical patient. In the illustrated embodiment, the suture anchor 66 is positioned on a rear edge of the header 22 and the suture anchor 68 is positioned on a top edge of the header 22. In alternative embodiments, the suture anchors 66 and 68 can be positioned at other locations on the header 22 as suitable for the application. In further alternative embodiments, header 22 can have fewer or greater than two suture anchors. For example, the header 22 can include a third suture anchor (not shown) positioned on a front edge of the header 22, opposite of the suture anchor 66. When the pulse generator 12 is implanted into the medical patient, a surgeon can choose to use one of the multiple suture anchors deemed most appropriate for the application. Alternatively, the surgeon can choose to attach both suture anchors 66 and 68 (or all three suture anchors in embodiments with three suture anchors) in order to provide further support to the pulse generator 12 in the patient. Attaching via multiple suture anchors can be beneficial in applications where the specific position and/or orientation of the pulse generator 12 is important. Moreover, attaching via multiple suture anchors can be beneficial for reducing the risk of malfunction in a case of twiddler's syndrome, whereby a patient undesirably manipulates the pulse generator 12 in a way that spins the pulse generator 12 within the patient's body which can result in the twisting and/or dislodging of one or more of the leads 14 and 16 (shown in FIG. 1) and/or causing undesirable nerve stimulation.

Figure 2B:
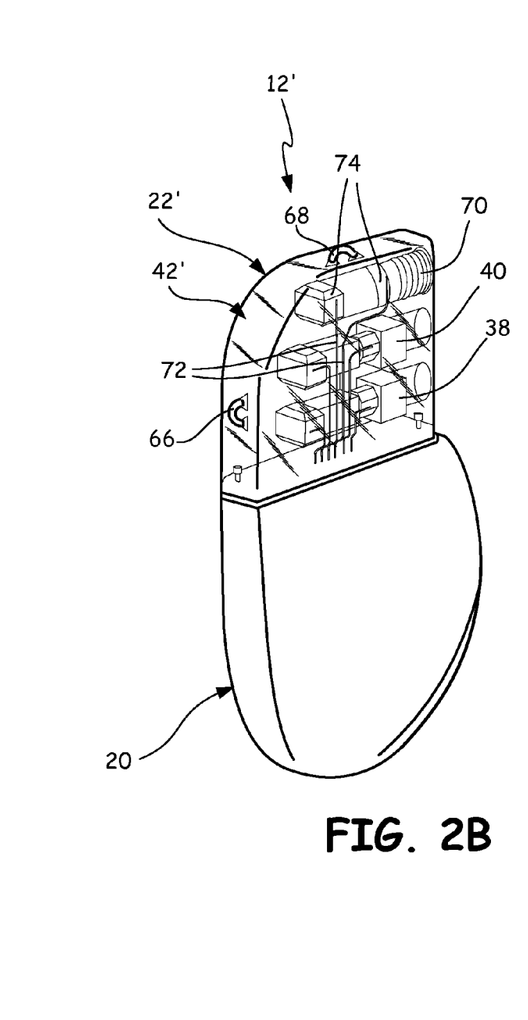
FIG. 2B is a perspective view of another embodiment of a pulse generator for use in the CRM system of FIG. 1, with a transparent header body.

FIG. 2B is another perspective view of a pulse generator 12', which is similar to the pulse generator 12 (shown in FIG. 2A) except that the pulse generator 12' has a header body 42' that is transparent. Because the header body 42' is transparent, the cores 38 and 40, as well as another core 70, are visible. A plurality of electrical leads 72 connect pulse generator circuitry (not shown) within the housing 20 to electrical contacts 74 on the cores 38, 40, and 70. Thus, the pulse generator 12' can transmit electrical signals to and from leads (such as the leads 14 and 16, shown in FIG. 1) connected to the header 22'.

Although the header 22' is shown in FIG. 2B as having three cores (the cores 38, 40, and 70) for connecting to three leads (not shown), the header 22' can have one, two, or more than three cores as suitable for a particular application. The cores 38, 40, and 70 are illustrated as three distinct cores. Alternatively, the cores 38, 40, and 72 can be combined as a single core having multiple receptacles (such as the receptacles 44, 46, and 48 as shown in FIG. 2A).

Figure 3:
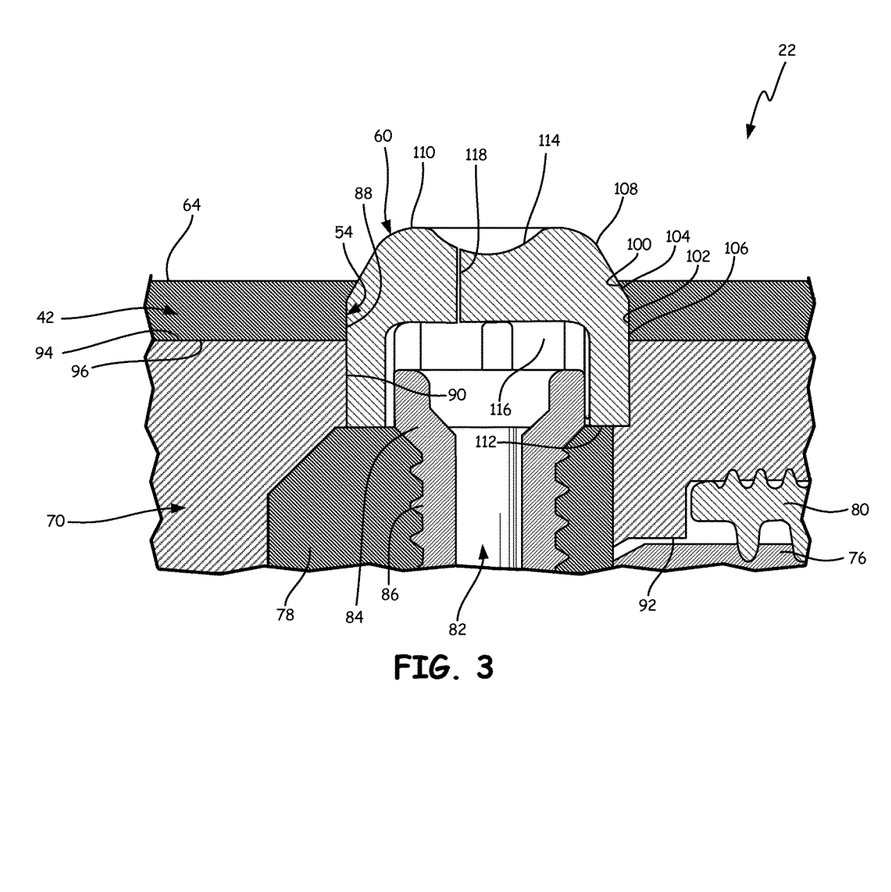
FIG. 3 is a sectional view of a portion of one embodiment of the header body.

FIG. 3 is a sectional view of the header 22, showing the header body 42, the core 70, and the plug 60. The core 70 contains a lead bore cavity 76 and a tip block 78. An inner seal 80 provides a substantially fluid tight seal between the core 70 and the lead bore cavity 76. A threaded fastener 82 has a head 84 connected to a threaded shaft 86. The threaded fastener 82 is a set screw threadedly engaged with the tip block 78. The threaded fastener 82 can be tightened so as to fasten a lead terminal pin on a proximal end of an electrical lead (such as the leads 14 and 16 of FIG. 1) in the lead bore cavity 76. The threaded fastener 82, the tip block 78, and the lead bore cavity 76 can be made of electrically conductive metal so as to conduct signals to and from the electrical lead.

The hole 54 is a set screw hole that extends through the header 22. The hole 54 includes a header body hole 88 extending through and defined by the header body 42 and a core hole 90 extending through and defined by the core 70. The core hole 90 extends from a core interior 92 to the core outer surface 94. The header body hole 88 extends from a body inner surface 96, which is adjacent and molded to the core outer surface 94, to the indented surface 64 (or the outer surface 62) of the header body 42. The header body hole 88 has a hole outer portion 100 and a hole inner portion 102. The indented surface 64 of the header body 42 is nearer the hole outer portion 100 than the hole inner portion 102. A distance across the hole outer portion 100 is less than a distance across the hole inner portion 102.

The plug 60 is positioned in the header body hole 88 and the core hole 90. The plug 60 has a plug outer portion 104 aligned with the hole outer portion 100 and has a plug inner portion 106 aligned with the hole inner portion 102. A distance across the plug outer portion 104 is substantially equal to the distance across the hole outer portion 100. A distance across the plug inner portion 106 is substantially equal to the distance across the hole inner portion 102. Thus, the distance across the plug outer portion 104 is less than the distance across the plug inner portion 106.

In the illustrated embodiment, the plug 60 is substantially cylindrical at plug inner portion 106 and then tapers from the plug inner portion 106 to the plug outer portion 104 such that the plug 60 is substantially frustoconical at the plug outer portion 104. Thus, the distance across the plug outer portion 104 is a diameter of the plug outer portion 104 and the distance across the plug inner portion 106 is a diameter of the plug inner portion 106. The header body hole 88 is formed to the shape of the plug 60 where the header body 42 contacts the plug 60. Thus in the illustrated embodiment, the header body hole 88 is substantially cylindrical at the hole inner portion 102 and then tapers from the hole inner portion 102 to the hole outer portion 100 such that the header body hole 88 is substantially frustoconical near the hole outer portion 100. The header body 42 is an epoxy outer layer overmolded over the core 70 that covers some but not all of a frustoconical surface 108 of the plug 60 at the plug outer portion 104. In alternative embodiments, the plug 60 can have a shape different than as illustrated. For example, the plug 60 can have multiple cylindrical sections connected by a radial step. Alternatively, the plug 60 can have a larger, smaller, or additional frustoconical portion. Alternatively, the plug 60 can have a shape substantially that of a square pyramid.

In the illustrated embodiment, the plug 60 has a plug top 110 and a plug bottom 112 opposite the plug top 110. The plug 60 defines a concave indentation 114 on the plug top 110 and a plug cavity 116 on the plug bottom 112. A slit 118 extends from the concave indentation 114 on the plug top 110, through the plug 60, to the plug cavity 116. The head 84 of the threaded fastener 82 is positioned at least partially in the plug cavity 116. Under normal operation, the slit 118 is substantially closed to seal and limit fluid flow through the plug 60. The slit 118 is deformable, allowing a tool (not shown) to be inserted through the slit 118 into the head 84 of the threaded fastener 82 to turn the threaded fastener 82. When the tool is removed, the slit 118 can resiliently return to its original, sealed configuration. The plug 60 can be made of a resilient polymer material suitable for sealing the hole 54.

The shapes of the plug 60 and the header body hole 88 can help retain the plug 60 in the hole 54. Because the distance across the plug outer portion 104 (and across the hole outer portion 100) is smaller than the distance across the plug inner portion 106 (and the hole inner portion 102), the plug 60 can be prevented from falling out of the header body hole 88 during normal operation of the pulse generator 12 (shown in FIG. 1). The plug 60 can be retained in the header body hole 88 without using medical adhesive between the plug and either the header body hole 88 or the core hole 90.

Figure 4:
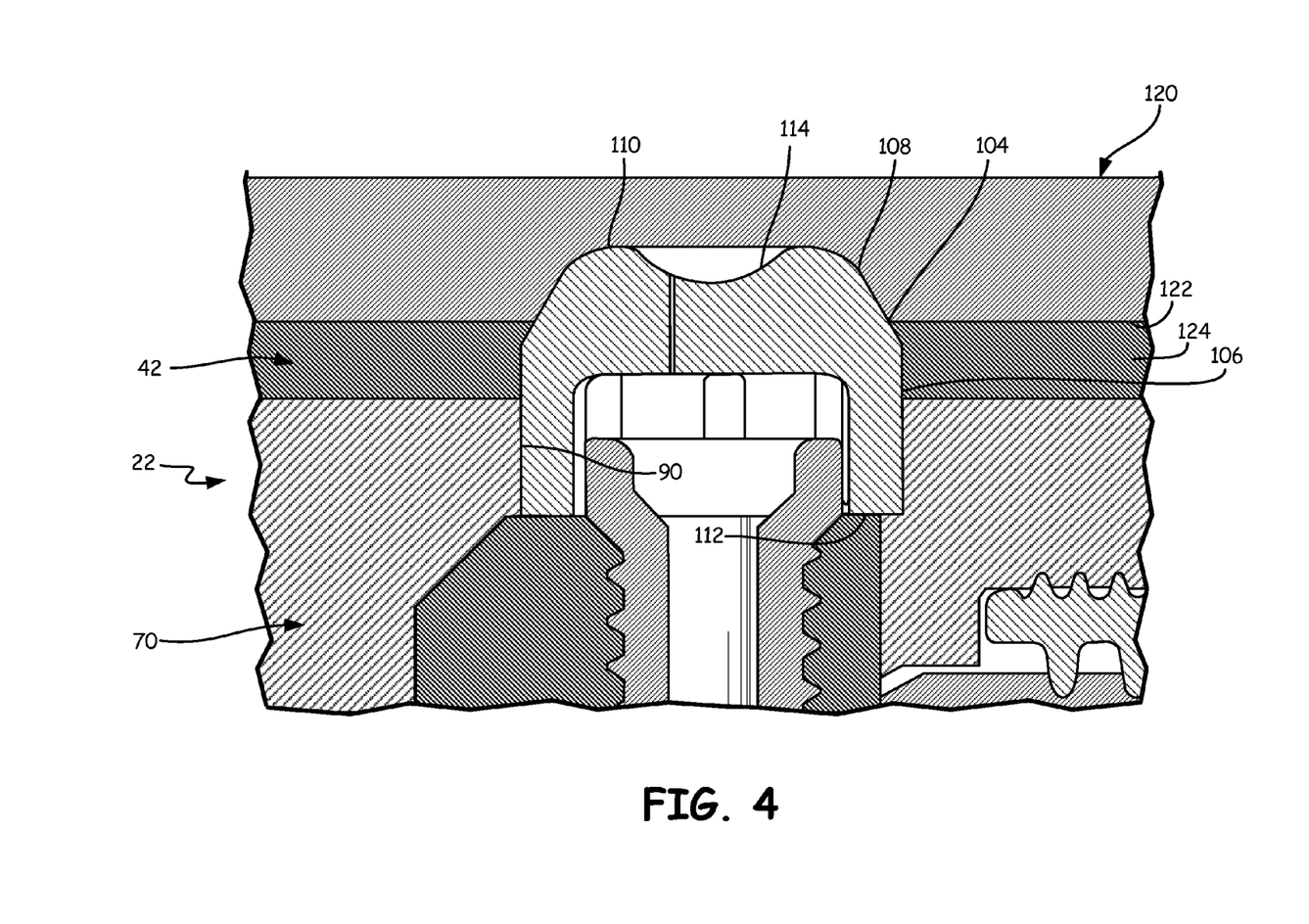
FIG. 4 is a sectional view of the portion of the header body of FIG. 3 positioned in a mold.

FIG. 4 is a sectional view of a portion of the header 22, showing the header body 42, the core 70, and the plug 60, in a mold 120. The mold 120 has an inner surface 122 defining a header mold cavity 124 that has substantially the same shape as the header 22. The mold 120 can also define a housing cavity (not shown) configured to hold the housing 20 adjacent the header mold cavity 124. In one embodiment, the mold 120 can be formed of a silicone material. For example, the mold 120 can be made from a two part liquid injection silicone. In another embodiment, the mold 120 can be made from a compression molded silicone. In another embodiment, the mold 120 can be made from a room temperature vulcanizing silicone. In one embodiment, the mold 120 can consist or consist essentially of silicone. In alternative embodiments, the mold 120 can include other materials in addition to or instead of silicone. In a further alternative embodiment, the mold 120 can be formed of another material suitable for the application.

The header 22 can be formed by first premolding the core 70 using another mold (not shown). The core 70 can be molded in the shape substantially as illustrated, including the core hole 90. The housing 20 can be positioned at least partially in the housing cavity of the mold 120, adjacent the header mold cavity 124, and the core 70 can be positioned in the header mold cavity 124. The plug 60 can be positioned in the mold 120 such that the plug bottom 112 is in the core hole 90, the plug top 110 is adjacent the inner surface 122, and the plug outer portion 104 and the plug inner portion 106 are in the header mold cavity 124 between the mold 120 and the core 70.

Header material can then be injected into the header mold cavity 124 to form the header body 42 such that the header 22 is attached to the housing 20. The header material can flow over the core 70 to substantially encapsulate the core 70. The header material can flow around the plug 60 so as to retain the plug 60 in the header 22 at a surface of the header 22. The header material can partially cover the plug 60, including a portion of the frustoconical surface 108, and leave a portion of the plug 60, including the plug top 110 and the concave indentation 114, exposed. Thus, the plug top 110 extends out of the header 22 when the header material solidifies. The pulse generator 12 can then be removed from the mold, with the header 22 attached to the housing 20 and the plug 60 retained in the header 22. The plug 60 is thus attached and retained in the header 22 without use of medical adhesive in an interface between the plug 60 and the core 70 or between the plug 60 and the header body 42. In one embodiment, the header material can be an epoxy resin. In an alternative embodiment, the header material can be another material suitable for the application. In the illustrated embodiment, the plug 60 is held between the core 70 and the mold 120 with the plug bottom 112 of the plug 60 seated in the core hole 90. In an alternative embodiment, the core 70 can be omitted and the plug 60 can be seated in a version of the header 22 configured without cores.

Figure 5A:
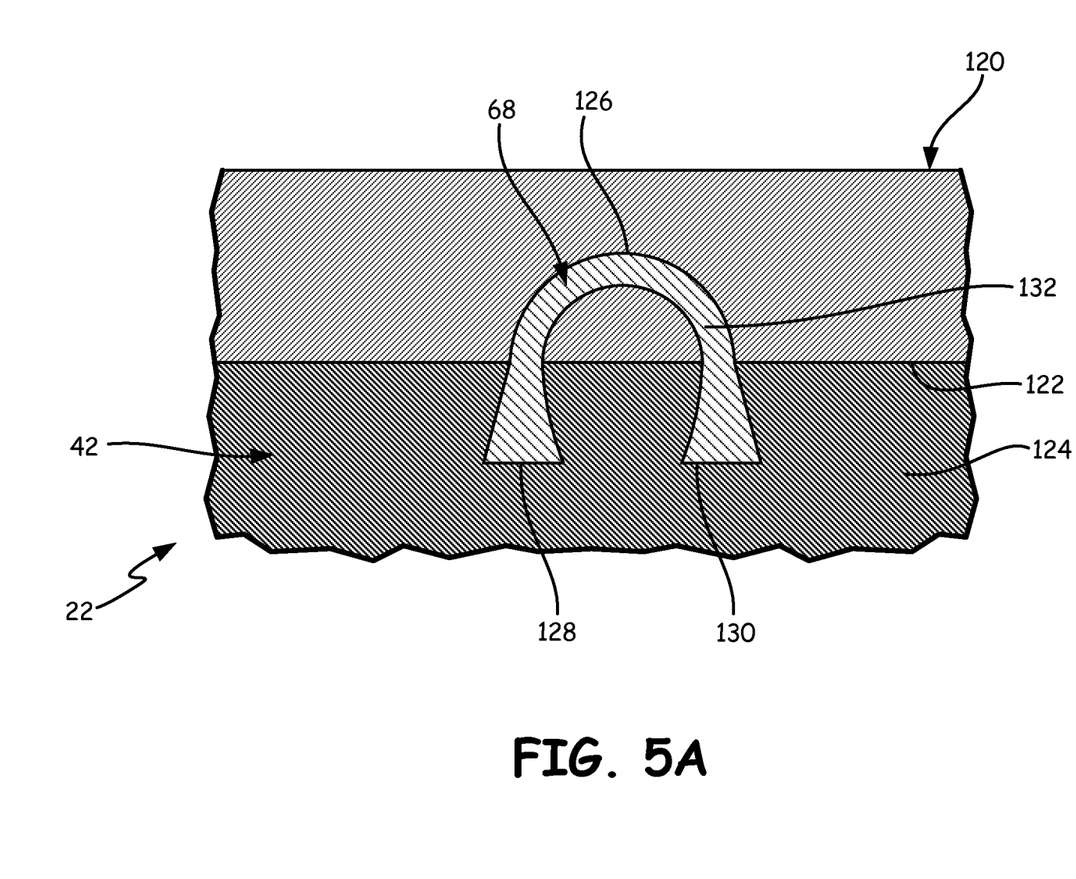
FIG. 5A is a sectional view of the header body and one embodiment of a suture anchor positioned in the mold.

FIG. 5A is a sectional view of the header 22, showing the header body 42 and the suture anchor 68 in the mold 120. In the illustrated embodiment, the suture anchor 68 is a monofilament line that includes a suture loop 126 between two anchor ends 128 and 130. In the illustrated embodiment, the anchor ends 128 and 130 are reverse tapered, having a larger diameter at the anchor ends 128 and 130 than near the suture loop 126. The anchor ends 128 and 130 are potted in the header body 42 so as to retain the suture anchor 68 to the header body 42. The suture loop 126 extends out of the header body 42, allowing the suture loop 126 to be sutured to tissue in the body of the patient. The suture loop 126 can be made of a material suitable to be pierced by a suture needle when being sutured to body tissue. In the illustrated embodiment, the suture anchor 68 is made of a monofilament polymer material. In an alternative embodiment, the suture anchor 68 can be a braided thread. In various embodiments, the suture anchor 68 can be made of other materials suitable for the application, including materials that are absorbable and/or materials that are non-absorbable by the body of the patient.

The suture anchor 68 can be attached to the header body 42 in a manner similar to that of attaching the plug 60 (shown in FIGS. 3 and 4) to the header body 42. The housing 20 can be positioned at least partially in the housing cavity of the mold 120, adjacent the header mold cavity 124. The suture anchor 68 can be positioned in the mold 120 such that the anchor ends 128 and 130 are in the header mold cavity 124 and the loop 126 is positioned in a suture anchor cavity 132 defined by the inner surface 122 of the mold 120. In the illustrated embodiment, the suture anchor cavity 132 is substantially arch-shaped. The suture anchor 68 can be held relatively tightly in the suture anchor cavity 132, with the suture loop 126 adjacent the inner surface 122. The suture anchor 68 can be used in headers 22 with and without cores, such as the core 70. In embodiments with the core 70, the core 70 can also be positioned in the header mold cavity 124.

Header material can then be injected into the header mold cavity 124 to form the header body 42 such that the header 22 is attached to the housing 20. The header material can flow over the core 70 to substantially encapsulate the core 70. The header material can flow around the suture anchor 68 so as to retain the suture anchor 68 in the header 22 at a surface of the header 22. The header material can partially cover the suture anchor 68, including the anchor ends 128 and 130, and leave a portion of the suture anchor 68, including the suture loop 126, exposed. Thus, the suture loop 126 extends out of the header 22 when the header material solidifies. The pulse generator 12 can then be removed from the mold, with the header 22 attached to the housing 20 and the suture anchor 68 retained in the header 22.

Figure 5B:
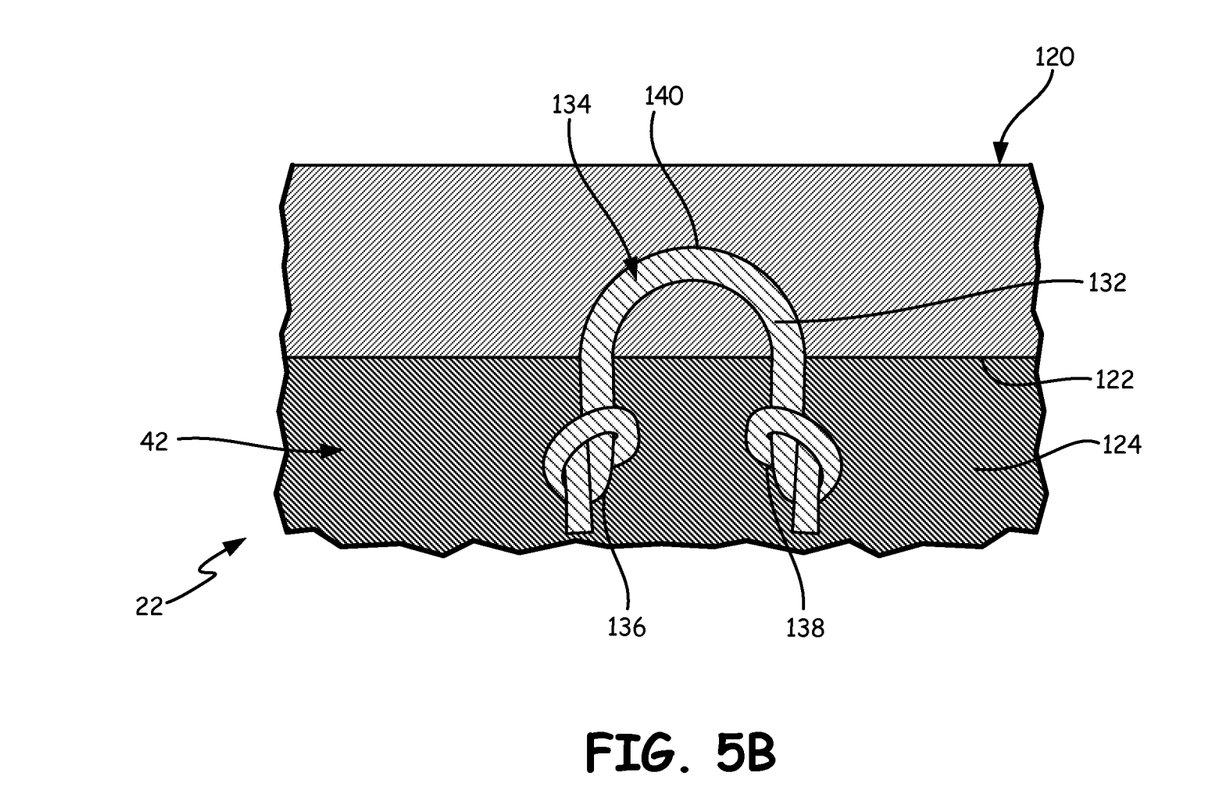
FIG. 5B is a sectional view of the header body and another embodiment of a suture anchor positioned in the mold.

FIG. 5B is a sectional view of the header 22, showing the header body 42 and a suture anchor 134 in the mold 120. The suture anchor 134 is substantially the same as the suture anchor 68 (shown in FIG. 5A), except that the suture anchor 134 is tied to form knots at anchor ends 136 and 138 prior to positioning the suture anchor 134 in the mold 120. Because the anchor ends 136 and 138 are knotted and potted in the header body 42, the suture anchor 134 can be retained in the header body 42. A suture loop 140 extends between the anchor ends 136 and 138. Like the suture loop 126 (shown in FIG. 5A), the suture loop 140 extends out of the header body 42, allowing the suture loop 140 to be sutured to tissue in the body of the patient. The suture anchor 134 can be attached to the header body 42 using the same mold 120 and method described above with respect to the suture anchor 68.

Figure 5C:
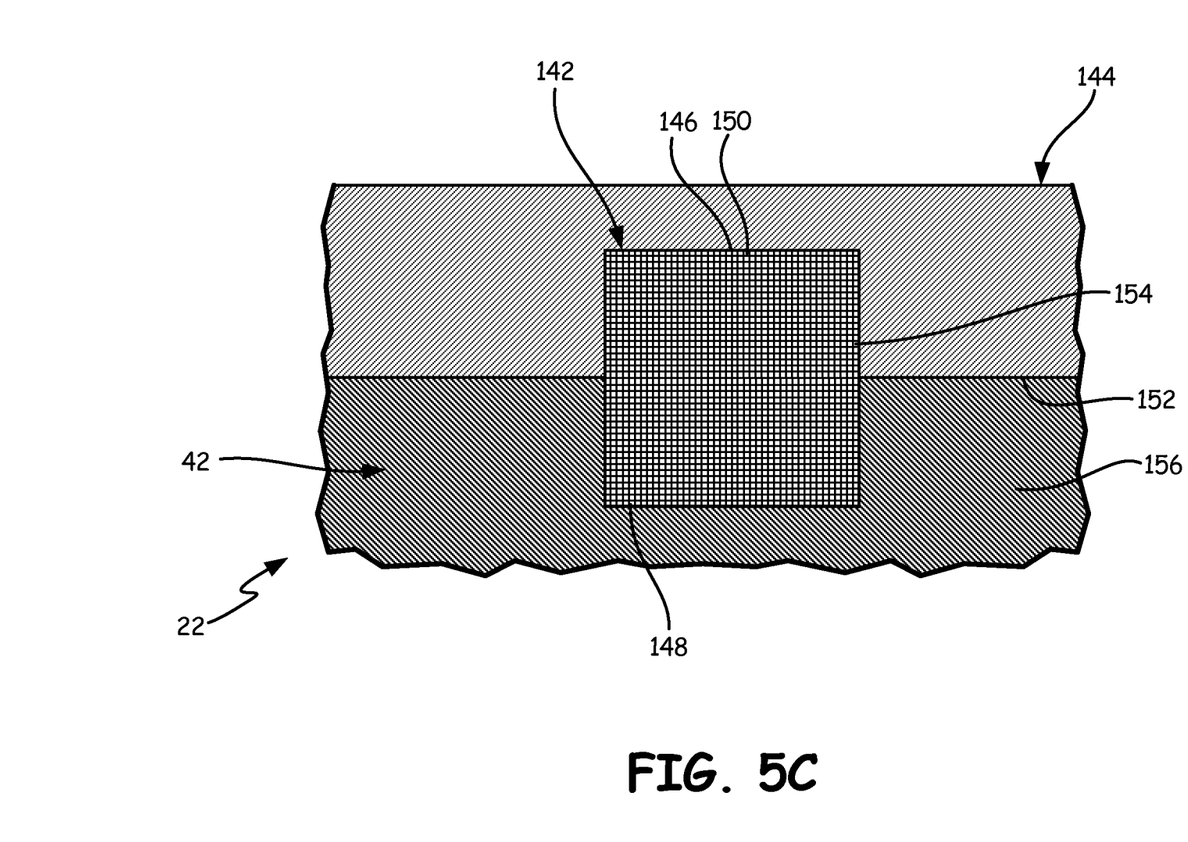
FIG. 5C is a sectional view of the header body and another embodiment of a suture anchor positioned in the mold.

FIG. 5C is a sectional view of the header 22, showing the header body 42 and a suture anchor 142 in a mold 144. The suture anchor 142 is substantially similar to the suture anchors 68 and 124 (shown in FIGS. 5A and 5B), except that the suture anchor 142 a flexible membrane. In the illustrated embodiment, the suture anchor 142 is a substantially rectangular sheet with a suture portion 146 and an anchor portion 148. The anchor portion 148 is potted in the header body 42 to retain the suture anchor 142 in the header body 42. The suture portion 146 extends out of the header body 42, allowing the suture portion 146 to be sutured to tissue in the body of a medical patient. In the illustrated embodiment, the suture anchor 142 is a knitted mesh with a plurality of pores 150. In the illustrated embodiment, the pores 150 are positioned in both the suture portion 146 and the anchor portion 148. The pores 150 in the suture portion 146 can allow for the suture portion 146 to be pierced by a suture needle. The pores 150 in the anchor portion 148 can allow for header material to flow into the pores 150 to provide structural support for retaining the suture anchor 142 in the header body 42. In alternative embodiments, the suture anchor 142 can have a different shape and configuration suitable for the application.

In one embodiment, the suture portion 146 of the suture anchor 142 can be relatively short, but long enough to allow the suture portion 146 to be attached to tissue via sutures. In another embodiment, the suture portion 146 can be relatively long. For example, in one embodiment the suture portion 146 can have sufficient length to be able to wrap around a bundle of leads (such as the leads 14 and 16 shown in FIG. 1) and then be attached to tissue via sutures. In that embodiment, the suture anchor 142 can be used to attach both the pulse generator 12 (shown in FIG. 1) and the bundle of leads to tissue.

In some embodiments, the suture portion 146 of the suture anchor 142 can be coated with antibiotics that dissolve when implanted in the medical patient. Antibiotics can thus be delivered locally at a suture location to help reduce risk of infection due to implantation. In alternative embodiments, antibiotics can be omitted.

The suture anchor 142 can be attached to the header body 42 using the mold 144, which is similar to the mold 120 (shown in FIGS. 5A and 5B), except that the mold 144 has an inner surface 152 that defines a suture anchor cavity 154 sized and shaped for the suture anchor 142. In the illustrated embodiment, the suture anchor cavity 154 is substantially rectangular with a relatively shallow depth so as to hold the suture anchor 68 relatively tightly in the suture anchor cavity 154, with the suture portion 146 adjacent the inner surface 152. The inner surface 152 of the mold 144 also defines a header mold cavity 156. Header material can then be injected into the header mold cavity 156 to form the header body 42 such that the header 22 is attached to the housing 20 and the suture anchor 142 is attached to the header body 42.

Thus, the above description includes methods to mold components in place on a header body so as to be attached at a surface of the header body. These methods can be performed with seal plugs used to seal set screw holes. This can allow such seal plugs to be retained in the header body in a way that is relatively reliable and without use of medical adhesive. These methods can also be used to attach a suture anchor to the header body. Such suture anchors can take one of a number of configurations and can allow attachment at a variety of locations on the header body. Attaching suture anchors as described can allow for headers to be formed without including suture attachment holes extending through the header body. Use of a silicone mold and epoxy header material can allow the header to be reliably attached to the housing of the medical device and allow one or more components, such as seal plugs and suture anchors, to be reliably attached to a surface of the header in the same injection molding process.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable pulse generator comprising:
    a device housing containing pulse generator circuitry;
    a header including a header body hole, the header molded to the device housing and formed of an epoxy header material; and
    a seal plug having a first part molded in the epoxy header material to fix the seal plug to the header at a surface of the header and having a second part extending out of the epoxy header material, the seal plug positioned in a set screw hole that comprises the header body hole defined by the epoxy header material of the header, and wherein a distance across an outer portion of the header body hole is less than a distance across an inner portion of the header body hole.

2. The implantable pulse generator of claim 1, wherein the seal plug has a deformable slit extending through a top of the seal plug through which a tool can be inserted and that is substantially closed to seal and limit fluid flow through the seal plug when the tool is removed.

3. The implantable pulse generator of claim 1, wherein the seal plug is a suture anchor for attaching the header to tissue in a medical patient.

4. The implantable pulse generator of claim 1, wherein an interface between the seal plug and the header is substantially free of medical adhesive.

5. A pulse generator for a cardiac rhythm management system, the pulse generator comprising:
    a device housing;
    a header molded to the device housing, wherein the header is formed of an epoxy header material, wherein the epoxy header material defines a set screw hole, and wherein a distance across an outer portion of the set screw hole is less than a distance across an inner portion of the set screw hole;
    a set screw positioned in the header and aligned with the set screw hole; and
    a seal plug having a deformable slit extending through the seal plug for receiving a tool to tighten the set screw, wherein the seal plug is molded in the epoxy header material at a surface of the header to fix the seal plug to the header, and wherein a plug top of the seal plug extends out of the surface of the header.

6. The pulse generator of claim 5, wherein the seal plug has a tapered outer surface that engages an inner surface of the set screw hole.

7. The pulse generator of claim 6, wherein the tapered outer surface is a frustoconical surface, and the header has a frustoconical inner surface that engages the frustoconical outer surface of the seal plug and secures the seal plug in the header.

8. A pulse generator for a cardiac rhythm management system, the pulse generator comprising:
    a device housing;
    a header including a core and a header body, the header molded to the device housing, wherein the header body is formed of an epoxy header material, wherein the epoxy header material defines a set screw hole, and wherein the header includes a lip extending over the set screw hole;
    a set screw positioned in the header and aligned with the set screw hole; and
    a seal plug having a deformable slit extending through the seal plug for receiving a tool to tighten the set screw, wherein the seal plug is molded in the epoxy header material at a surface of the header to fix the seal plug to the header, and wherein the lip on the header secures the seal plug in the set screw hole.

* * * * *